United States Patent [19]

Constantz

[11] Patent Number: 5,034,059

[45] Date of Patent: Jul. 23, 1991

[54] COMPOSITION COMPRISING OCTACALCIUM PHOSPHATE CRYSTALS AND POLYPEPTIDE

[75] Inventor: Brent R. Constantz, Woodside, Calif.

[73] Assignee: Norian Corporation, Mountain View, Calif.

[21] Appl. No.: 312,866

[22] Filed: Feb. 17, 1989

[51] Int. Cl.$^5$ .................... C08K 3/32; C09D 177/02; C09K 3/00

[52] U.S. Cl. ............................ 106/161; 128/DIG. 8; 252/183.13; 424/423; 424/484; 623/16

[58] Field of Search ............ 252/183.13; 128/DIG. 8; 623/16; 424/423, 484; 106/161

[56] References Cited

U.S. PATENT DOCUMENTS

| | | | |
|---|---|---|---|
| 3,959,192 | 3/1975 | Delfosse et al. | 521/14.5 |
| 4,264,493 | 4/1981 | Battista | 623/16 X |
| 4,321,042 | 3/1982 | Scheicher | 433/201.1 |
| 4,481,175 | 10/1983 | Shinji et al. | 423/308 |
| 4,503,157 | 3/1985 | Hatahira | 501/1 |
| 4,659,617 | 9/1985 | Fujii et al. | 428/221 |
| 4,693,986 | 1/1987 | Vit et al. | 501/1 |
| 4,776,890 | 10/1988 | Chu | 623/16 X |
| 4,880,610 | 11/1989 | Constanz | 623/16 X |

FOREIGN PATENT DOCUMENTS 3339996  4/1983  Fed. Rep. of Germany.

OTHER PUBLICATIONS

Napper and Smythe, *J. Dent. Res.* (1966), 45:1775–1783.
Deutsch and Sarig, *Journal of Crystal Growth* (1977), 42:234–237.
Jarcho, *Clinical Orthopedics and Related Research* (1981), 157:259–278.
Okazaki et al., *Journal of Biomedical Materials Research* (1982), 16:851–860.
Okazaki et al., *Caries Res.* (1984), 18:499–504.
Okazaki et al., *J. Dent. Res.* (1981), 60:845–849.
Ducheyne in *J. Biomed. Mater. Res.; Applied Biomaterials* (1987), 21:219–236.
LeGeros in *Calcified Tissue International* (1985), 37:194–197.
LeGeros in *Journal of Crystal Growth* (1972), 13(14):476–480.
LeGeros et al., *Scanning Electron Microscopy* (1984), IV:1771–1777.
Monma et al., *J. Chem. Tech. Biotechnol.* (1981), 31:15–24.

Primary Examiner—Richard D. Lovering
Attorney, Agent, or Firm—Bertram I. Rowland

[57] ABSTRACT

Octacalcium phosphate and hydroxyapatite are provided, where octacalcium phosphate is produced as novel single crystals and organized polycrystalline structures that are non-dense. The crystals serve as fibers, which find application in a wide variety of applications as well as coatings of prosthetic devices or other materials which may have physiological application.

2 Claims, No Drawings

COMPOSITION COMPRISING OCTACALCIUM PHOSPHATE CRYSTALS AND POLYPEPTIDE

INTRODUCTION

1. Technical Field

The technical field of this invention is the preparation of calcium phosphate single crystals and non-dense organized polycrystalline structures of the same having low amounts of intercrystalline contacts and high bulk porosity, particularly octacalcium phosphate. The compositions find use in a wide variety of prosthetic devices and full bone replacement.

2. Background

Biocompatible materials are an important adjunct in the treatment of individuals having a wide variety of bone diseases. Calcium phosphate minerals are of great interest in being biocompatible in providing for a range of physical and chemical properties. Hydroxyapatite has been of particular interest, since it is a major inorganic component of bones and teeth. Octacalcium phosphate has also been indicated as involved in the production of bone, although its presence in significant amounts has not been established. There is a belief that octacalcium phosphate may be an intermediate in the formation of calcium hydroxyapatite in vivo.

There is, therefore, great interest in being able to synthetically produce products which will approximate the properties of naturally occurring bone. These compositions may find use in coatings of prosthetic devices, as bone grafting material, as replacements of portions of bone, as reinforcements, and the like.

A wide variety of compatible materials are reported for use as bone substitutes, as bone supports, and the like. Numerous reports have described methods of preparing various inorganic biocompatible materials in various forms, particularly hydroxyapatite. For a number of reasons, these materials have not found general acceptance and lack many desirable features. There is, therefore, substantial interest in being able to develop processes for the production of biocompatible calcium compounds and using these compositions by themselves or in conjunction with various other biocompatible polymeric materials, or as coatings of formed objects to be used in vivo.

U.S. Pat. No. 4,693,986 provides a description of the state of the art concerning apatite products as bone substitutes. Okazakai, J., et al, Biomedical Materials Research (1982), 16:851-860; Okazakai, J., et al, Caries Res. (1984), 18:499-504; and Okazakai, J., et al, J. Dent. Res. (1981), 60:845-849, described the preparation of hydroxyapatite needle-like crystals. Calcium phosphate fibers are described in a number of Japanese patents including: JP57/117621; JP53/111000; JP53/110999; JP61/201019; and JP58/054023. German Publication No. DE 33 39 996 describes calcium carbonate needles and particles. U.S. Pat. No. 3,959,192 describes calcium carbonate particle fillers. Napper and Smythe, J. Dent. Res. (1966), 45:1775-1783, describe the preparation of hydroxyapatite crystals using calcium acetate. For a review of calcium phosphate ceramics as hard tissue prosthesis, see Jarcho, Clinical Orthopedics and Related Research (1981), 157:259-278. Discussions of octacalcium phosphate may be found in LeGeros et al, Scanning Electron Microscopy (1984) 4:1771-1777 and references cited therein.

SUMMARY OF THE INVENTION

Methods and compositions are provided for the production of single crystals, polycrystalline spherulites, and fabrics of octacalcium phosphate having a specified range of crystal morphologies which are homogenous and controllable through engineering of the mother liquor, and the use of the compositions as bone or bone-like material substitutes.

DESCRIPTION OF THE SPECIFIC EMBODIMENTS

Methods are provided for the production of octacalcium phosphate (OCP) in the form of single crystals and organized polycrystalline structures of the same composition. The polycrystalline structure of the subject composition differs from other forms of ceramic calcium phosphate bone substitute in that they are non-dense and single crystals touch in less than 20% of their surfaces. Methods are also provided for transformation of the subject octacalcium phosphate to hydroxyapatite without altering the crystal morphology, as well as the use of the compositions in a variety of applications involving bone or bone-like materials.

Under a specific set of circumstances defined by agitation, pH, temperature, and reactant source, OCP can be engineered to form single crystals, spherulites, ropes (spaghetti-like), or fabrics. The later three forms are polycrsytalline.

Single crystals (or whiskers) can range in shape from broad plates to blades to needles. These are formed by varying rates of growth along the three triclinic axes of OCP. Plates and blades will generally be 0.1 $\mu$m to 4 $\mu$m thick, 1.0 $\mu$m to 200 $\mu$m wide, and 20 $\mu$m to 20 mm long. Needles will generally be 0.1 $\mu$m to 10 $\mu$m in diameter and 10 $\mu$m to 5 mm in length. All morphologies mentioned above are single crystals.

The single crystal forms may form a organized polycrystalline structures which are typically ropes, fabrics or spherulites. Ropes (spaghetti) generally have a thickness of 10-100 single crystals and infinite lengths. Fabrics usually occur in a thickness of 10-100 single crystals lying in the plane of the fabric.

The compositions will be substantially homogeneous in chemical composition ($\geq 95\%$), mineralogically pure (same crystal structure ($\geq 95\%$)) and homogeneous morphologically, generally varying by not more than about $\pm 20\%$ from the average in each dimension.

The spherulites are characterized by having an open structure and of a size in the range of about 400 $\mu$m to 4 mm for octacalcium phosphate. The whiskers will generally be of a size in the range of about 20 $\mu$ to 2 mm for the octacalcium phosphate. The spherulites provide for very high surface areas, where about 1 to 99% have the fibers in a plane which cuts through the spherulite. OCP and other calcium phosphates are covalently bonded materials and have a net charge on their outer crystal surfaces so that the enhanced surface charge binds polar materials, particularly proteins to enhance adherence. OCP and hydroxyapatite (HA) have a net negative charge which attracts positively charged collagen. Negatively charged polypeptides adhere to collagen. The average number of blades or rays radiating from the center will generally be in the range of about 10 to 100. The blades will usually have a width to thickness ratio of from about 1 to 100. The OCP may be transformed to HA having substantially the same dimensions.

The single crystals and organized polycrystalline structures will for the most part have a uniform composition, both mineralogically and morphologically, although mixtures may be prepared which have various calcium phosphate ratios, as well as the presence of other anions. Both the single crystals and the organized polycrystalline structures are able to interact with each other to provide an extended network, when combined with other materials resulting in more useful physical properties. In addition, the fibers may be further characterized by having a crystal structure where the c-axis is along the length of the single crystal while the a and b axes are along the cross-section of the fiber. Other characteristics which provide for the desired physical properties of the subject fibers are lack of fluid inclusions from the mother liquor, and uniform chemistry (i.e. Ca:P ratio), mineralogy, size, and shape. Different chemistries, mineralogies, sizes and shapes behave differently in vivo.

The method for preparing the subject fibers involves the slow bringing together at an elevated temperature and at a mildly acidic pH of a water soluble calcium source and a water soluble phosphate source. During the addition, the pH is maintained by the addition of an appropriate acidic or alkaline medium. Relatively dilute solutions are employed which support nucleation and slow growth of the spherulites. One of the reactants may be slowly added to the other reactant with stirring or the two reactants may be introduced simultaneously into a medium at the appropriate pH and temperature at a high dilution with agitation. The final volume will usually be 2 to 50% greater than the volume of the two solutions added, usually about 5 to 30% greater. The reactant being added may be preheated or used at ambient temperature, generally being added at a temperature in the range of at least about 20°, to usually about 90° C. The reaction will be maintained at a temperature in the range of about 60° to 80° C., more usually in the range of about 60° to 75° C. The pH will be maintained in the range of about 4 to 7.0, preferably about 4.5 to 6.5, more preferably about 5, where the addition of base or acid will be employed to maintain the pH as required.

The concentration of the calcium source when added to a phosphate solution will generally be in the range of about 1–10 g/l, where the rate of addition will generally be in the range of about 100–500 ml/h. The phosphate solution will generally be at a concentration in the range of about 1–10 g/l. Varying rates and amounts will be used depending on total volumes. Once the desired temperature has been reached, the addition of the reagent(s) to the reaction vessel may begin, while pH and temperature are maintained and monitored. Conveniently, a cover may be employed to prevent loss of water. For example, polyethylene balls in sufficient number to cover the surface may be used. When the addition is complete, the heating is terminated and stirring is continued until the solution cools to room temperature. The mixture may then be filtered and the precipitate dried as convenient.

The stoichiometry for the calcium and phosphate sources should be about 1.33:1 although it may vary from about 1:1 to 2:1.

The particular compounds used as the source of the phosphate and the calcium are not critical, although some compositions will be preferred over others. As the source of phosphate, alkali metal or ammonium salts may be used, particularly sodium. As the calcium salt, various organic and inorganic anions providing water soluble salts may be employed, such as acetate, citrate, nitrate, chloride, malonate, tartrate, fumarate. The choice of counterions will be determined to some degree on the interaction of the counterions, so as to avoid any precipitation or involvement of the counterions in the crystal structure.

The octacalcium phosphate may be readily hydrolyzed into hydroxyapatite in accordance with known ways. See, e.g., LeGeros et al, supra. The octacalcium phosphate may be readily transformed to hydroxyapatite by heating in the presence of water for sufficient time for the octacalcium phosphate to form hydroxyapatite. Generally, the conditions will be temperatures in the range of 170° C. to 280° C., and times in the range of 1 h to 24 h. The transformation may also be achieved by putting OCP in an oven for at least about 24 h at 170°–220° C. The octacalcium phosphate can be completely transformed to hydroxyapatite without altering its morphology.

The single crystals and organized polycrystalline structures may be used in a variety of ways. The fibers may be combined with a variety of materials to be used as a composite for a resorbable matrix. Collagen, particularly soluble collagen, may be combined and crosslinked with the subject fibers. In addition, a polyanionic material may be employed, where the collagen will be from about 1 mg/ml to 50 mg/ml, the calcium phosphate from about 0.1 g/ml to 1.0 g/ml and the polyanionic from about 10 $\mu$g/ml to 100 mg/ml. Polyanionic compounds may include polysulfonates and polycarboxylates. Of particular interest, are heparin fragments, polysulfonated sugars, e.g., SOS, (sucrose octasulfate) polyaspartic acid, polyglutamic acid, combinations thereof, or the like.

The mixture may be made homogeneous by sonication in vacuo. In addition, various bone growth factors may be employed, such as TGF-$\beta$, bone growth factor, bone morphogenetic factor, combinations thereof, or the like. Generally, the growth factors will be present in from about 1 $\mu$g/ml to 1 mg/ml.

For various implant devices, which may be of a variety of materials, particularly metals or hardened plastics, e.g. Co-Cr Alloy, Ti-Steel, Polysulfone, the article may be coated with the subject crystals. For example, a biocompatible epoxy resin, such as, Hardman 13215 may be coated onto the device and the fibers blown on to the resin as a fine coating. Alternatively, the article may be implanted with metal ions on the surface, such as calcium ions, and then introduced into the reaction medium during the preparation of the calcium phosphate crystals. Thus, the crystals will grow onto the surface and be bonded onto the surface through the ionic bonds to the implanted metal ions. Alternatively, the crystals may be plasma coated onto the article, where the article is an electrically conducting metal or can be made electrically conducting. The current will be 600 to 800 Amps, and the pressure of the gas will vary depending on the nature of the gas. Generally, argon will be used at a pressure in the range of about 40 to 50 psi, while helium will be used in the range of about 80 to 100 psi. The gases used carry the fibrous calcium phosphate onto the surface of the article. Areas to remain uncoated may be masked for protection.

The subject crystals will also be used with various thermoset or thermo-plastic compositions, such as epoxy and polysulfone. These compositions may be used as bone graft extenders, so that they may be mixed with natural bone, used to fill in spaces between bone grafts and the host bone, fill cracks, or the like.

The following examples are offered by way of illustration and not by way of limitation.

EXPERIMENTAL

EXAMPLE 1

Solutions were prepared of 1.32 g of calcium acetate and 250 ml of double distilled (dd) water, 1.04 g of sodium phosphate monobasic in 250 ml dd water and 100 ml of dd water waS added to a 600 ml flask covered with foil. The calcium acetate solution was heated. The 600 ml flask was heated to 69.5° C. and 50% acetic acid added to pH 3.8. Addition was begun when the temperature of the calcium acetate solution was 74.6° C. The pH was allowed to rise to 5, while the temperature fluctuated between 60° to 70° C. in the reaction mixture. At one point the temperature of the calcium acetate solution rose to 99° C., but then dropped to 73.5° C. The simultaneous addition of the calcium acetate and sodium phosphate solutions required 50 min. The solution was allowed to cool to room temperature, where white crystals of about 0.5 mm diameter formed. The crystals were filtered, washed 3×35 ml dd water, 4×35 acetone, followed by 400 ml dd water. The crystals were then vacuum dried and infrared analysis showed the product to be substantially octacalcium phosphate.

EXAMPLE 2

Solutions were prepared of 3.1 g sodium phosphate monobasic in 750 ml dd water and 3.96 g calcium acetate monohydrate in 750 ml dd water. Into a two liter beaker was introduced 350 ml dd water and 28 polyethylene balls and the beaker covered with a composite of foil/fiberglass material/foil for insulation. A stir bar was introduced into the beaker for agitation and heating and agitation begun. When the solution had reached 70° C., and the pH 5.0 by addition of 5% acetic acid, the two solutions were added simultaneously at a flow rate of 285 ml/h. When addition was complete, the heat and stirring was turned off and the solution was allowed to cool to room temperature. The reaction mixture was then filtered through Whatman #52 filter paper. followed by washing 6×300 ml dd water. The precipitate was collected and dried in an oven at 110° C.

EXAMPLE 3

Octacalcium phosphate (OCP) (prepared as described above) was transformed into hydroxyapatite as follows. Into 350 ml of dd water was added 0.45 g of OCP in a beaker and the beaker covered with a foil cover. The temperature was raised to 76° C. and a 5% ammonium hydroxide solution added to raise the pH to about 8. The temperature was maintained in the range of about 80° to 82°, while the pH fluctuated between 7.4 and 8.0 over a period of 150 minutes. At the end of this time, stirring was stopped, the cover removed and the reaction mixture allowed to cool. An aliquot was taken, rinsed with acetone (35 ml) and the product analyzed by infrared spectroscopy. The yield was calculated to be 64.9% of hydroxyapatite from the OCP.

It is evident from the above results that the subject spherulitic compositions, either as octacalcium phosphate or hydroxyapatite prepared therefrom, may find broad applications. The subject compositions may be used in conjunction with proteins, such as collagen to provide implants which form trabecular bone. The subject compositions may be coated onto various prosthetic devices to provide protective coatings which are biocompatible and provide for better acceptance of the prosthesis. The subject compositions may be used with collagen to form resorbable matrixes. The subject compositions may be combined with various thermoplastic and thermoset materials to produce isotropic composites, which may find use as bone cements, bioactive ceramics and to enhance the strength of various materials which may have physiological application.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A composition comprising octacalcium phosphate crystals and a polypeptide, said octacalcium phosphate crystals being substantially uniform single crystals and non-dense assemblages of polycrystalline structures in the form of spherulites, ropes (spaghetti) or fabrics, said crystals being produced by a method comprising:

combining at a temperature in the range of about 60°–90° C. in stoichiometric amount by simultaneous addition, aqueous solutions of calcium cation and phosphate anion to an aqueous medium maintained at a pH in the range of about 4 to 7 until addition is complete to produce a dispersion containing octacalcium phosphate; and cooling said dispersion, whereby octacalcium phosphate crystals form.

2. A composition according to claim 1, wherein said polypeptide is collagen.

* * * * *